United States Patent [19]

Lane, Jr.

[11] 4,139,569
[45] Feb. 13, 1979

[54] VAPOR PHASE CRACKING OF DICYCLOPENTADIENE AND SYNTHESIS OF 2,3-DIHYDROXYCYCLOPENTADIENE AND CYCLOPENTENE

[75] Inventor: Parley C. Lane, Jr., Cuyahoga Falls, Ohio

[73] Assignee: The B. F. Goodrich Company, Akron, Ohio

[21] Appl. No.: 851,034

[22] Filed: Nov. 14, 1977

[51] Int. Cl.$^2$ ........................ C07C 3/26; C07C 13/12
[52] U.S. Cl. ........................... 260/666 A; 260/666 P; 260/666 PY
[58] Field of Search ........................ 260/666 A, 666 D

[56] References Cited
U.S. PATENT DOCUMENTS
2,793,238  5/1957  Banes et al. ..................... 260/666 A Primary Examiner—Veronica O'Keefe
Attorney, Agent, or Firm—John H. Faro

[57] ABSTRACT

Improved process for vapor phase cracking of dicyclopentadiene and synthesis of 2,3-dihydrodicyclopentadiene therefrom. Initially, a feedstock consisting essentially of dicyclopentadiene and cyclopentene is subjected to thermocracking in the vapor phase, resulting in the conversion of dicyclopentadiene to monomeric cyclopentadiene. The presence of cyclopentene in the feed stock is believed to minimize coke formation on the interior walls of the cracking chamber. Subsequent selective catalytic hydrogenation of the resulting mixture converts substantially all of the monomeric cyclopentadiene to cyclopentene. The cyclopentene, prepared in the above manner, can be combined with additional quantities of dicyclopentadiene and the resultant mixture subjected to dimerization in the liquid phase at elevated temperatures, thereby forming the monomer, 2,3-dihydrodicyclopentadiene.

9 Claims, 1 Drawing Figure

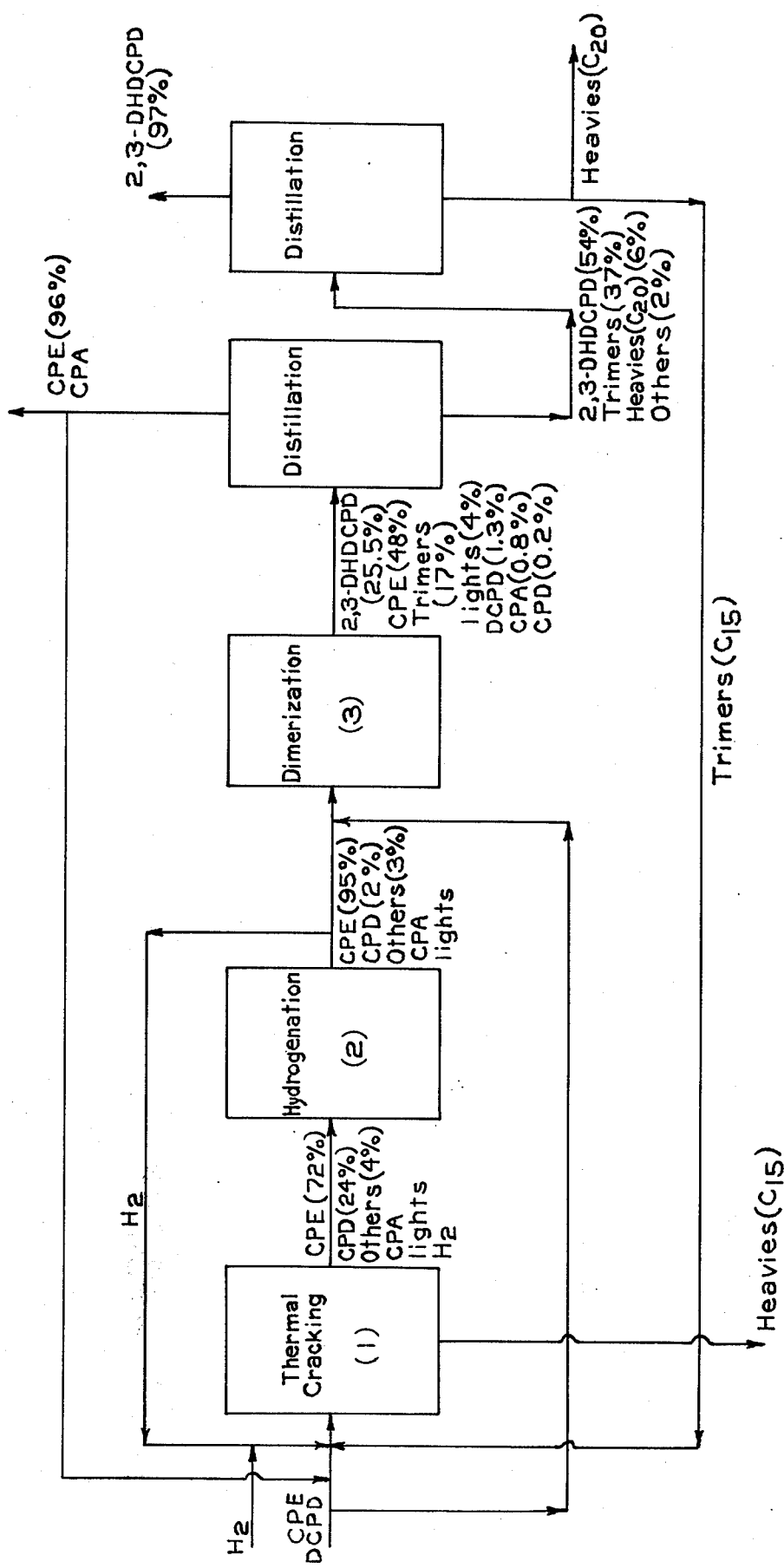

VAPOR PHASE CRACKING OF DICYCLOPENTADIENE AND SYNTHESIS OF 2,3-DIHYDROXYCYCLOPENTADIENE AND CYCLOPENTENE

BACKGROUND OF THE INVENTION

1. Field of the Invention

This invention is directed to a process. More specifically, this invention involves a novel process for vapor phase cracking of dicyclopentadiene and the synthesis of 2,3-dihydrodicyclopentadiene therefrom.

2. Description of the Prior Art

Dicyclopentadienes are of significant industrial value because of their ready conversion to either polymers or as intermediates in the preparation of a variety of desirable products (e.g. cyclopentadiene or cyclopentene). Dicyclopentadiene has been previously disclosed as a starting material in the synthesis of cyclopentene, U.S. Pat. No. 3,598,877. The '877 patent and the prior art discussed within patentees' specification teach that cracking of dimeric cyclopentadiene can take place in the presence of an auxiliary liquid, or in the vapor phase (with or without a hydrocarbon diluent). The presence of the auxiliary liquid during cracking of the dimer can adversely effect the yield. Because of such difficulties, industrial scale manufacture of monomeric cyclopentadiene is carried out via a vapor phase process. Such industrial processes will generally involve the vaporization of the dimer and conveyance of the resultant gaseous fluid through a heated tubular reactor wherein cracking to the monomer occurs. Since such depolymerization is reversible, even at low temperatures, the monomer must be fractionated rapidly if reasonable quantities of monomer are to be recovered.

Vapor phase cracking of cyclopentadiene dimer and higher polymers result in a greater conversion to the monomer, as compared to liquid phase cracking. However, there are serious drawbacks associated with vapor phase cracking; namely, the formation of coke on the interior walls of the cracking tubes. Inert gas addition to the vaporized dimer has been proposed to alleviate this difficulty, although Nelson et al (U.S. Pat. No. 2,801,270) indicated that the process may be operated efficiently without such inert gas addition, and that such addition may actually hinder the separation of the monomer from the other materials in the cracking reactor effluent.

The inventors of the process of patent '877 indicate that coke formation can be minimized during vapor phase cracking of cyclopentadiene dimer by the addition of a hydrocarbon diluent to the dicyclopentadiene feedstock. The hydrocarbon diluents suggested by patentees must satisfy very specific requirements regarding their inertness and heat of vaporization.

As is evident from the above discussion, vapor phase cracking of dicyclopentadiene is the more desirable of the other alternatives disclosed by the prior art insofar as the yields obtainable are more commercially acceptable. There is, however, the continuing problem of coincident coke formation within the cracking apparatus. The invention described in the '877 patent is significant in the sense that it goes a long way toward reducing coke formation, however, with the added disadvantage of introduction of materials into the feedstock which create downstream problems regarding their separation from the desired end product.

SUMMARY OF THE INVENTION

Accordingly, it is the object of this invention to remedy the above as well as related deficiencies in the prior art.

More specifically, it is the principle object of this invention to provide an improved vapor phase process for cracking dicyclopentadiene.

It is another object of this invention to provide an improved vapor phase process for cracking of dicyclopentadiene wherein the cyclopentadiene monomer can be readily separated from the effluent of the cracking process.

It is another object of this invention to provide an improved process for preparation of 2,3-dihydrodicyclopentadiene.

It is still yet another object of this invention to provide an improved process for preparation of 2,3-dihydrodicyclopentadiene wherein the 2,3-dihydrodicyclopentadiene can be readily separated from the other materials used in its preparation.

Still yet another object of this invention is to provide an improved continuous process for preparation of 2,3-dihydrodicyclopentadiene.

The above and related objects are achieved by providing a feedstock consisting essentially of dicyclopentadiene and cyclopentene. As a matter of convenience, hydrogen may be introduced into the process stream at the cracking stage. This feedstock is initially subjected to thermocracking in the vapor phase. The presence of cyclopentene (as a diluent) in the feedstock is believed responsible for a dramatic reduction in coke formation within the interior of the cracking apparatus. Moreover, the use of a cyclopentene diluent greatly simplifies subsequent separation of the resultant products of the cracking operation.

The above mixture can be thereafter contacted with an appropriate catalytic agent and the cyclopentadiene selectively hydrogenated to cyclopentene. Further processing of the cyclopentene in the liquid phase by contacting with appropriate quantities of cyclopentadiene in a dimerizer yields the monomer, 2,3-dihydrodicyclopentadiene.

BRIEF DESCRIPTION OF THE DRAWINGS

FIG. 1 is a schematic flow diagram of the process of this invention.

DESCRIPTION OF THE INVENTION INCLUDING PREFERRED EMBODIMENTS

In accordance with the process of this invention, a feedstock consisting essentially of dicyclopentadiene (DCPD) and cyclopentene (CPE) is introduced into a cracking furnace. Hydrogen can also be added to the feedstock at this stage. The addition of hydrogen to the feed has the effect of increasing the dilution of the relative concentration of DCPD in the cracker thereby further decreasing the incidence of coke formation. The relative concentrations of DCPD in the feed should be maintained at less than about 50 weight % and preferably in the range of from about 20 to about 30 weight %. Additional dilution of the DCPD below 20 weight % apparently neither reduces the incidence of coke formation nor the selectivity of the cracking reaction and thus does not materially enhance the efficiency of the process. The molar ratio of hydrogen to dicyclopentadiene in the feed to the cracking furnace may be varied within wide limits. Generally this ratio will be greater than 1.0.

A particularly desirable range of ratios for hydrogen to dicyclopentadiene lies between about 5.0 and 50.0. The preferred range of ratios is between about 8.0 and about 40.0.

The inlet portion of the furnace will preferably function as a preheater and vaporizer. Subsequent to vaporization of feedstock, it is channeled into the pyrolytic portion of the furnace wherein it undergoes thermocracking. The temperature prevailing within this pyrolytic chamber should be maintained in the range of from about 200° to 400° C., and preferably within a range of from about 250° to 350° C. The pressure maintained within the vapor phase cracking furnace will in all cases be superatmospheric, and will depend upon the amount of hydrogen in the feed as well as the temperature maintained therein. Under such temperature conditions, and for various hydrogen to dicyclopentadiene ratios, the pressure within the depolymerization furnace will generally lie between about 50 and about 500 p.s.i.g. The preferred operating pressure maintained in the cracking furnace is from about 75 to about 250 p.s.i.g.

Effluent from this furnace, after quenching, is separated into two phases: a vapor phase which contains cyclopentene (CPE), cyclopentadiene (CPD) and cyclopentane (CPA), and a second phase comprising unconverted dimer and/or refractory polymers. This latter phase is drawn off and discarded. The fraction from the pyrolytic chamber containing the CPE, CPD and CPA can be condensed to a liquid or fed directly as a vapor into the hydrogenation chamber, the latter practice being preferable. Preliminary to introduction of the CPE, CPD and CPA vapor stream into the hydrogenation reactor it is cooled to approximately 260° C.

The cyclopentene is thereafter selectively formed over a suitable hydrogenation catalyst. Where hydrogen is not already present in the vapor stream from the thermocracking unit, it must of course be added at this juncture. The volume of hydrogen introduced into the hydrogenation chamber is sufficient to convert substantially all the CPD to CPE and preferably is present in excess of stoichiometric quantities. During the selective hydrogenation of CPD to CPE large quantities of heat are also liberated. A variety of well known techniques may be employed to control the hydrogenation reaction exotherm. The other conditions prevailing during such hydrogenation are also conventional.

A number of catalysts are available which are effective for the selective hydrogenation of cyclopentadiene monomer produced in the cracking furnace. Sulfided nickel oxides are the preferred catalytic agents. Thus, nickel sulfide itself, as disclosed by Greensfelder (U.S. Pat. No. 2,402,493), or sulfided nickel, commercially available from Harshaw Chemical Company (Type Ni 0301 T Nickel — on alumina) provide the desired selective hydrogenation of the cyclopentadiene to cyclopentene with a minimum of cyclopentane formation.

The hydrogenation reaction may be carried out under pressure of from about 50 to about 250 p.s.i.g., and at a temperature in the range of from about 175° to about 350° C. Because, as mentioned earlier, a large exotherm occurs during the hydrogenation of the cyclopentadiene, some means must be employed to assist in the removal of heat generated during such reaction. One technique for controlling the temperature within hydrogenation reactor is to dilute the hydrogenation catalyst with an inert material whose concentration throughout the catalyst bed is uniform, or whose content is initially high and then decreases in the direction of flow. A second technique for controlling the exotherm involves the division of the cyclopentadiene monomer retrieved from the cracking furnace and the division of the total volume of catalyst into an equal number of streams and beds, respectively, and thereafter introduce the divided monomer streams below or between the separate beds.

Subsequent to the selective hydrogenation of monomeric cyclopentadiene (CPD) to cyclopentene (CPE) the effluent from the hydrogenation reactor is channeled to a dimerizer and additional dicyclopentadiene (DCPD) added. The materials introduced into the dimerizer are reacted in the liquid phase at a temperature in the range of from about 220° to 240° C. At such temperatures the DCPD is cracked to CPD which in turn undergoes a Diels-Alder addition reaction with CPE forming 2-3,dihydrodicyclopentadiene (2,3-DHDCPD).

The effluent from the dimerizer can be thereafter fed into a distillation column wherein the cyclopentene and cyclopentane are removed. The cyclopentene can be taken off or reintroduced into the reaction scheme by addition to the original feedstock. The residue remaining subsequent to separation of the cyclopentene is further fractionated thereby separating 2,3-dihydrodicyclopentadiene (2,3-DHDCPD) from the trimers remaining in the residue. The trimers can be similarly recycled back into the original feedstock mixture. Where trimers are recycled back into the feed, the temperature of the pyrolytic chamber must be adjusted accordingly since higher temperatures are required to effect cracking of these materials.

As is evident from the above discussion, the presence of cyclopentene in the original feedstock simplifies the separation of the various products at different stages of the reaction cycle. Moreover, this material is apparently responsible for minimizing coke formation during the thermocracking of the dicyclopentadiene, thus preventing fouling of the pyrolytic chamber of the cracking furnace. Coke formation is also effectively eliminated during the dimerization stage of the process.

EXAMPLES

The Examples which follow further define, describe and illustrate the improved processes of this invention. Apparatus and techniques used in such illustrations are standard or as hereinbefore described. Parts and percentages appearing in these Examples are by weight unless otherwise indicated.

EXAMPLE I

The process of this invention can be most readily exemplified by reference to FIG. 1. As shown in this illustration, a feed containing about 20 weight percent dicyclopentadiene in cyclopentene was introduced into a reactor concurrent with hydrogen and a minor amount of recycled cyclopentadiene trimers. The temperature of the reactor is maintained at about 260° C. After about 0.6 hours, the contents of the reactor were discharged, cooled and separated into two fractions. The lighter of the two fractions (cyclopentadiene, cyclopentene and cyclopentane) was condensed to a liquid and fed into a hydrogenation reactor. This liquid fraction was formed over a 5% palladium on alumina catalyst (poisoned with pyridine) at a temperature of about 32° C. and 65.3 p.s.i.g. hydrogen pressure for 450 minutes. The effluent from such hydrogenation was then discharged from the hydrogenation reactor and fed, in the liquid phase, into a dimerizer where it was contacted with dicyclopentadiene. Dicyclopentadiene was added to the dimerizer in an amount sufficient to create a CPE/CPD ratio of about 5:1 in the dimerization chamber. At the temperatures prevailing within this chamber (220°–240° C.) the dicyclopentadiene undergoes cracking to cyclopentadiene which in turn is reacted with cyclopentene to form 2,3-dihydrodicyclopentadiene (2,3-DHDCPD). After about 0.6 hours, the contents of the dimerizer are discharged and separated into a light and heavy fraction. The light fraction containing predominantly CPE is recycled back into the original feed. The heavier fraction was fractionated into 2,3-DHDCPD, CPD trimers and polymer residues. The CPD trimers thus recovered, were also recycled back into the original feed.

EXAMPLE II

The procedures of Example I are repeated, except for carrying out the hydrogenation of the cyclopentadiene in the vapor phase. The results obtained are substantially equivalent to those of Example I.

The flow diagram shown in FIG. 1. is merely illustrative of the process of this invention. The yields indicated at various stages of the reaction sequence are those obtainable under what are believed to be optimum conditions. This flow diagram is, however, intended as simply representative of one of the more preferred embodiments of this invention and not necessarily commensurate with the scope thereof, which is delineated in the following claims.

I claim:

1. A process for vapor phase cracking of dicyclopentadiene, said process comprising:
   providing a feedstock consisting essentially of dicyclopentadiene and cyclopentene; and
   introducing said feedstock in the vapor phase into a pyrolytic chamber, said pyrolytic chamber being maintained at a temperature in the range of from about 200° to 400° C. and the residence time of the feedstock in said chamber being sufficient to effect cracking of at least some of said dicyclopentadiene to cyclopentadiene.

2. The process of claim 1 wherein the pyrolytic chamber is maintained at superatmospheric pressures.

3. The process of claim 1 wherein the temperature of the pyrolytic chamber is maintained within a range of from about 300° to 350° C.

4. The process of claim 1 wherein the feedstock contains a minor amount of dicyclopentadiene and a major amount of cyclopentene.

5. A process for preparation of 2,3-dihydrodicyclopentadiene, said process comprising:
   providing a feedstock consisting essentially of dicyclopentadiene and cyclopentene;
   introducing said feedstock in the vapor phase into a pyrolytic chamber, said pyrolytic chamber being maintained at a temperature in the range of from about 200° to 400° C. and the residence time of the feedstock in said chamber being sufficient to effect cracking of at least some of said dicyclopentadiene to cyclopentadiene
   hydrogenating the lighter of the two fractions of an effluent, obtained from pyrolysis of the feedstock, to a suitable hydrogenation catalyst and hydrogen thereby converting substantially all of the monomeric cyclopentadiene of said effluent to cyclopentene; and
   introducing the effluent produced during the said hydrogenation and a source of cyclopentadiene into a liquid phase dimerizer, the temperature within said dimerizer being maintained within a range of from about 200° to 240° C.

6. The process of claim 5 wherein the products of said dimerization are separated from one another by distillation.

7. The process of claim 6 wherein at least some of the products recovered from distillation are recycled back into the initial feedstock.

8. A process for vapor phase cracking of dicyclopentadiene, said process comprising:
   providing a feedstock consisting essentially of dicyclopentadiene, cyclopentene and hydrogen; and
   introducing said feedstock in the vapor phase into a pyrolytic chamber, said pyrolytic chamber being maintained at a temperature in the range of from about 200° to 400° C. and the residence time of the feedstock in said chamber being sufficient to effect cracking of at least some of said dicyclopentadiene to cyclopentadiene.

9. A process for preparation of 2,3-dihydrodicyclopentadiene, said process comprising:
   providing a feedstock consisting essentially of dicyclopentadiene, cyclopentene and hydrogen;
   introducing said feedstock in the vapor phase into a pyrolytic chamber, said pyrolytic chamber being maintained at a temperature in the range of from about 200° to 400° C. and the residence time of the feedstock in said chamber being sufficient to effect cracking of at least some of said dicyclopentadiene to cyclopentadiene.
   subjecting the lighter of the two fractions of an effluent, obtained from pyrolysis of the feedstock, to selective hydrogenation thereby converting substantially all of the monomeric cyclopentadiene of said effluent to cyclopentene; and
   introducing the effluent produced during the said hydrogenation and a source of cyclopentadiene into a liquid phase dimerizer, the temperature within said dimerizer being maintained within a range of from about 220° to 240° C.

* * * * *